United States Patent
Gugaratshan et al.

(10) Patent No.: US 7,428,838 B2
(45) Date of Patent: Sep. 30, 2008

(54) CALIBRATION FOR AN OIL-CONSUMPTION-MEASUREMENT SYSTEM

(75) Inventors: Kulasegaram Gugaratshan, Peoria, IL (US); Orhan Altin, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 126 days.

(21) Appl. No.: 11/513,106

(22) Filed: Aug. 31, 2006

(65) Prior Publication Data

US 2008/0053209 A1    Mar. 6, 2008

(51) Int. Cl.
    *G12B 13/00* (2006.01)
(52) U.S. Cl. .................. 73/1.06; 73/1.02; 73/23.31; 73/23.33
(58) Field of Classification Search .......... 73/1.02, 73/1.06, 23.31, 23.32, 3.33, 31.05, 116, 117.2, 73/117.3, 119 R
See application file for complete search history.

(56) References Cited

U.S. PATENT DOCUMENTS

| | | | |
|---|---|---|---|
| 2,999,383 A | | 9/1961 | Bryan |
| 3,471,696 A | | 10/1969 | Mayer et al. |
| 4,048,497 A | | 9/1977 | Fritzsche |
| 4,321,056 A | | 3/1982 | Dimitroff |
| 4,370,060 A | | 1/1983 | Murase et al. |
| 4,990,780 A | | 2/1991 | Lee et al. |
| 5,117,680 A | * | 6/1992 | Colvin ............. 73/116 |
| 5,129,257 A | | 7/1992 | Carduner et al. |
| 5,445,964 A | | 8/1995 | Lee et al. |
| 5,531,105 A | | 7/1996 | Leong et al. |

(Continued)

FOREIGN PATENT DOCUMENTS

GB    2 051 354 A    1/1981

(Continued)

OTHER PUBLICATIONS

SAE Technical Paper Series, 902113, "On-Line Diesel Engine Oil Consumption Measurement", Bailey et al., presented Oct. 22-25, 1990, pp. 27-39.

(Continued)

*Primary Examiner*—David A. Rogers
(74) *Attorney, Agent, or Firm*—Finnegan, Henderson, Farabow, Garrett & Dunner

(57) ABSTRACT

A method for a method for calibrating a system configured to analyze exhaust gas produced by a fluid consuming source is disclosed. The method includes directing a first flow of exhaust gas toward an analyzer that is configured to measure at least one component. The method also includes establishing a first value indicative of a measurement of the at least one component within the first flow of exhaust gas. The method also includes removing a first quantity of fluid from the fluid consuming source and delivering a second quantity of fluid into the first flow of exhaust gas. The second quantity of fluid is a portion of the first quantity of fluid. The method also includes at least partially combusting the first flow of exhaust gas and the first quantity of fluid upstream of the analyzer and establishing a second value indicative of a measurement of the at least one component within the exhaust gas and the at least a portion of the first quantity of fluid. The method further includes calculating a calibration coefficient for the system as a function of a difference between the first value and the second value.

20 Claims, 3 Drawing Sheets

U.S. PATENT DOCUMENTS

| | | | | |
|---|---|---|---|---|
| 6,079,251 A | * | 6/2000 | Gaultier et al. | 73/23.31 |
| 7,244,395 B2 | * | 7/2007 | Olstowski | 422/80 |
| 2002/0053334 A1 | * | 5/2002 | Chamberlin et al. | 123/196 R |
| 2005/0042763 A1 | * | 2/2005 | Anderson et al. | 436/137 |
| 2005/0268692 A1 | * | 12/2005 | Delvigne et al. | 73/23.31 |

FOREIGN PATENT DOCUMENTS

| | | | |
|---|---|---|---|
| GB | 2 350 888 A | | 12/2000 |
| JP | 54042541 A | * | 4/1979 |
| JP | 55-139914 | | 11/1980 |
| JP | 56-132415 | | 10/1981 |

OTHER PUBLICATIONS

SAE Technical Paper Series, 920652, "On-Line Oil Consumption Measurement and Characterization of an Automotive Gasoline Engine by $SO_2$ Method", Ariga et al., presented Feb. 24-28. 1992, pp. 1-12.

SAE Technical Paper Series, 1999-01-3461, "Real-Time Steady-State Oil Consumption Measurement on Commerical Sl-Engine", Froelun, presented Oct. 25-28, 1999, pp. 1-10.

SAE Technical Paper Series, 860545, "Measurement of Oil Consumption of Diesel Engine by S-Trace Method", Iizumi et al., presented Feb. 24-28, 1986, pp. 1-9.

SAE Technical Paper Series, 860544, "Investigation of the Transient Oil Consumption of Engine by the Newly Developed Oil Consumption Meter", Maeda et al., presented Feb. 24-28, 1986, pp. 1-6.

* cited by examiner

CALIBRATION FOR AN OIL-CONSUMPTION-MEASUREMENT SYSTEM

TECHNICAL FIELD

The present disclosure relates generally to calibration, and more particularly, to a calibration apparatus and method for an oil-consumption-measurement system.

BACKGROUND

Combustion engines, e.g., diesel engines, gasoline engines, natural gas engines, and other engines known in the art, often consume, e.g., burn, oil during operation. A variation in oil consumption is typically an indication of one or more engine problems or undesirable engine performance. These problems or undesirable engine performance may decrease the life of the engine, engine components, and/or associated systems. A method of monitoring oil consumption may include monitoring and measuring the amount of sulfur present within engine exhaust. In such a method, the sulfur present in the engine fuel is usually less than 1-2 parts per million (ppm) on a weight-weight ratio and it is typically assumed that the significant source of sulfur present in the engine exhaust is caused by burnt engine oil. Because the measured amounts of sulfur in the engine exhaust are typically small, e.g., 30 parts per billion (ppb) on weight-volume ratio, calibration of the sulfur measuring system is required to insure accurate correlation between the measured amounts of sulfur and oil consumption.

One calibration method is described in SAE Paper 1999-01-3461 ("the '461 paper"). In the method of the '461 paper, a known quantity of sulfur dioxide is injected directly into a sulfur analyzer in order to calibrate the system. The sulfur analyzer then establishes a reading or series of readings for the known quantity of sulfur dioxide. Any difference between the readings and the known quantity is determined to be the calibration error. Depending on the system, the sulfur analyzer can be adjusted to zero out the error, e.g., rotating a dial to reset a baseline measurement, or the testing output can be corrected to eliminate the error, e.g., subtracting the calibration error from subsequently determined readings.

The calibration method of the '461 paper assumes that no variances exist between the calibration method and the testing method and, thus, does not account for environmental factors that differ from the calibration location and the testing location. Additionally, the method of the '461 paper calibrates the measurement device, e.g., an analyzer, by comparing a known amount of sulfur dioxide with a reading, which corrects potential errors with the analyzer but may not account for other system and/or environment factors when the analyzer is used to measure the sulfur present in engine exhaust.

The disclosed system is directed to overcoming one or more of the shortcomings set forth above.

SUMMARY OF THE INVENTION

In one aspect, the present disclosure is directed to a method for calibrating a system configured to analyze exhaust gas produced by a fluid consuming source. The method includes directing a first flow of exhaust gas toward an analyzer that is configured to measure at least one component. The method also includes establishing a first value indicative of a measurement of the at least one component within the first flow of exhaust gas. The method also includes removing a first quantity of fluid from the fluid consuming source and delivering a second quantity of fluid into the first flow of exhaust gas. The second quantity of fluid is a portion of the first quantity of fluid. The method also includes at least partially combusting the first flow of exhaust gas and the first quantity of fluid upstream of the analyzer and establishing a second value indicative of a measurement of the at least one component within the exhaust gas and the at least a portion of the first quantity of fluid. The method further includes calculating a calibration coefficient for the system as a function of a difference between the first value and the second value.

In another aspect, the present disclosure is directed to a system for calibrating a measurement system operatively connected to a source producing exhaust and configured to direct a portion of the exhaust toward an analyzer to detect at least one component of the exhaust. The system for calibrating includes a vessel configured to contain a sample volume of fluid and a pump configured to pressurize the sample volume of fluid. The system also includes a coupling configured to fluidly connect the system for calibrating to the measurement system and a flow controller configured to control the quantity of fluid communicated from the pump toward the coupling. The system also includes a fluid passageway fluidly communicating the vessel, the pump, the coupling, and the flow controller

DETAILED DESCRIPTION

Figure 1:
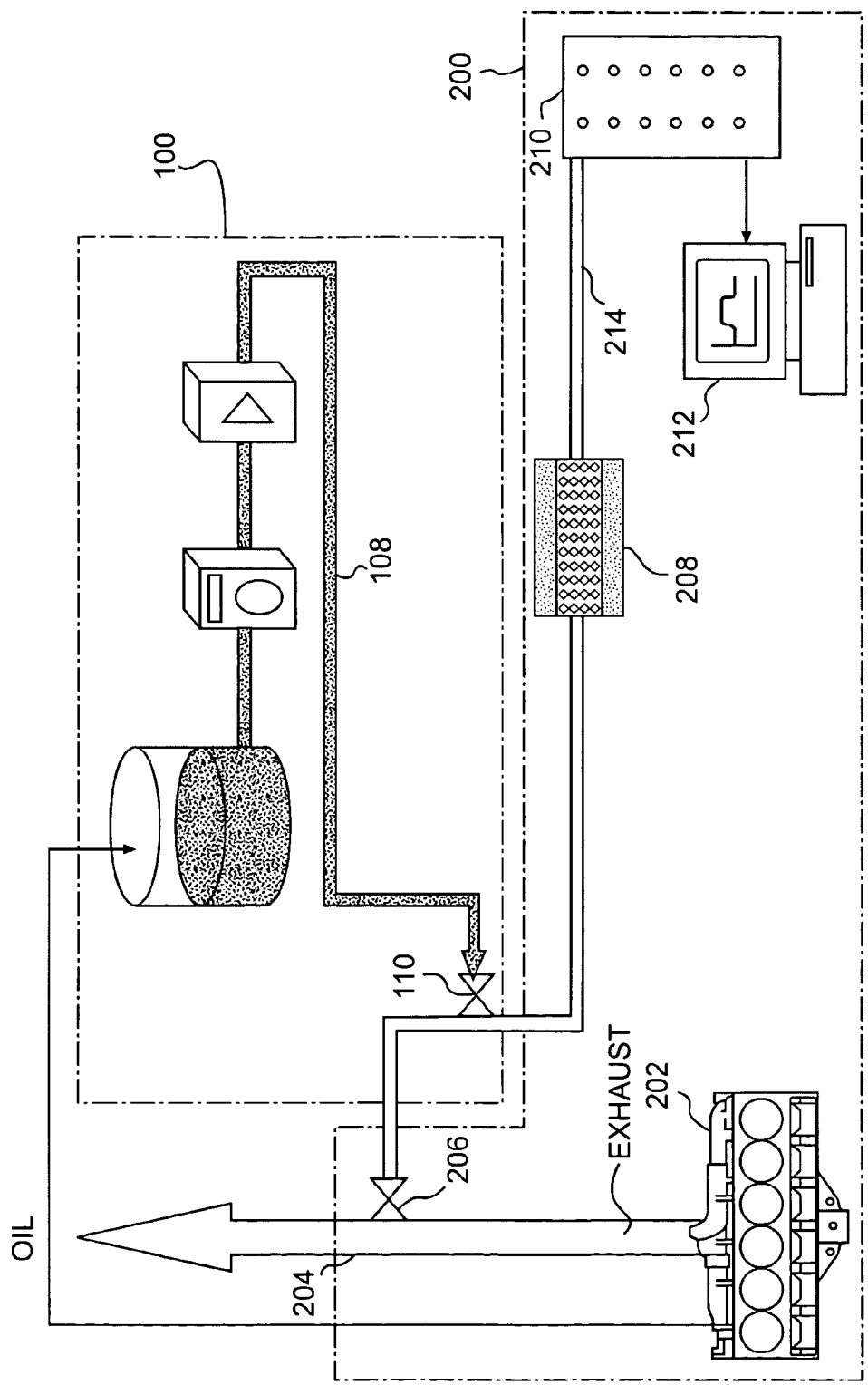
FIG. 1 is a diagrammatic illustration of an exemplary calibration system in accordance with the present disclosure.

FIG. 1 illustrates an exemplary calibration apparatus 100 for a system 200 that may be configured to measure oil consumption 200. Apparatus 100 may include a vessel 102 configured to contain a calibration sample, a pump 104 configured to pressurize the sample mixture, and a flow controller 106. A fluid passageway 108 may interconnect one or more components of apparatus 100 and may be configured to communicate the calibration mixture therebetween. Apparatus 100 may also include a coupler 110 to connect apparatus 100 with system 200. System 200 may include a source 202 utilizing oil and producing an exhaust 204, a control valve 206, a combustion chamber 208, an analyzer 210, and a computer 212. A fluid passageway 214 may interconnect one or more components of system 200 and may be configured to communicate exhaust therebetween.

Vessel 102 may be configured to contain the calibration sample, e.g., a mixture of oil, e.g., oil from source 202, and one or more additives or diluents, e.g., inert liquids. Specifically, vessel 102 may include an open vessel, e.g., a beaker, a flask, or other vessel suitable for containing a liquid calibration sample, or a closed vessel, e.g., a sealed flask or other vessel suitable for containing a gaseous calibration sample. Vessel 102 may also be configured to receive and contain a discrete amount of a calibration sample or may be configured to receive a continuous stream of the calibration sample. It is contemplated that the oil may be removed from source 202 and delivered to vessel 102 in any suitable manner known in the art, e.g., draining oil into an intermediate container and subsequently communicating the oil into vessel 102. It is also contemplated that any type or amount of additives or diluents may be combined with any amount of oil to, for example, decrease the viscosity of the oil, reduce the volatility of the oil, and/or adjust any other characteristic of the oil, as desired. It is further contemplated that vessel 102 may include one or more devices, e.g., a magnetic stir bar or platform vibrator, configured to mix or maintain motion of the calibration sample.

Pump 104 may be configured to pressurize the calibration sample. Pump 104 may include any type of pump such as, for example, a fixed or variable displacement pump. Pump 104 may establish and thus direct a flow of the calibration sample to flow controller 106 and to one or more other downstream components of apparatus 100. It is contemplated that pump 104 may, for example, include Monostato® Economy E-Series Peristaltic Pumps and may pressurize the calibration sample to a pressure of approximately 10 psi above ambient.

Flow controller 106 may be configured to regulate the flow of the pressurized calibration sample. Specifically, flow controller 106 may be configured to provide a predetermined amount of the calibration sample toward coupler 108. Flow controller 106 may control the flow of the pressurized calibration sample by any suitable method, such as, for example, by volume or by mass, as is known in the art. It is contemplated that flow controller 106 may be a Coriolus-type mass flow controller, e.g., a Brooks® QUANTIM® Coriolis Mass Flow Meter/Controller.

Fluid passageway 108 may be situated to fluidly connect and thus communicate the calibration sample from vessel 102 to pump 104, flow controller 106 and toward coupler 110. Fluid passageway 108 may be rigid or flexible and may be composed of any suitable material, e.g., stainless steel or other adequately corrosion resistive material. It is contemplated that fluid passageway 108 may be internally coated or lined with silicon and/or other suitable material to reduce reaction with or deposition on of substances within the calibration sample.

Coupler 110 may be configured to fluidly connect apparatus 100 to system 200. Coupler 110 may be connected to one end of fluid passageway 108 and may include a needle-like tip configured to be inserted into a corresponding coupling component in system 200. For example, coupler 110 may be a quick-connect fitting, a tube fitting, a cannula, a needle or any other suitable device for interconnecting apparatus 100 and system 200 and fluidly communicating the pressurized calibration sample thereto.

Source 202 may include any oil consuming and exhaust producing device, such as, for example, a combustion engine. Specifically, source 202 may include one or more combustion chambers configured to convert potential energy within fuel into kinetic energy. The operation of the combustion chambers is well known in the art and as such is not further described. Source 202 may consume, e.g., combust or partially combust, oil configured to lubricate one or more moving parts of the combustion chambers. For example, oil may enter the combustion chambers and may be exposed to the high temperatures therein and may be burned along with the fuel supplied to the combustion chamber. Source 202 may produce exhaust 204 which may include by-products of both the burnt fuel and the burnt oil and, specifically, may include sulfur by-products from the burnt oil. It is contemplated that exhaust 204 may include any type of by-products known in the art.

Valve 206 may include any conventional valve configured to selectively divert a portion of exhaust 204 toward analyzer 210. Specifically, valve 206 may include a bore and a spool movable between a first position substantially blocking the flow of exhaust 204 toward analyzer 210 and a second position allowing a maximum flow of exhaust 204 toward analyzer 210. Valve 206 may be a variable valve configured to selectively divert a variable amount of exhaust 204 between substantially no flow and a maximum flow or valve 206 may be a fixed valve configured to selectively divert either substantially no flow or a constant predetermined amount of flow. It is contemplated that valve 206 may be interconnected within an exhaust conduit configured to collect and communicate exhaust 204 from source 202 toward one or more downstream components, e.g., catalytic converters, or the environment. It is also contemplated that valve 206 may be, for example, a stop cock on which passageway 214 may be connected, a control valve threadingly connectable to the exhaust conduit and/or to passageway 214, and/or may be any other suitable device configured to divert a portion of exhaust 204 toward analyzer 210.

Combustion chamber 208 may include a heat source configured to combust the portion of exhaust 204 diverted by valve 206 and/or the calibration sample communicated to system 200 via coupler 110. Specifically, combustion chamber 208 may include an ignition source, e.g., a flame, to combust one or more components of exhaust 204, e.g., carbon dioxide, unburned hydrocarbons, or other by-products of source 202, and/or the calibration sample, e.g., the oil sample. It is contemplated that combustion chamber 208 may be configured to partially and/or completely combust the diverted portion of exhaust 204 and/or the calibration sample.

Analyzer 210 may be any conventional sulfur analytic tool configured to measure sulfur and/or sulfur compounds and produce sulfur readings indicative thereof. Specifically, analyzer 210 may be configured to determine the amount, e.g., mass, volume, or percentages thereof, of sulfur present within the diverted and combusted exhaust 204 and the combusted calibration sample. For example, analyzer 210 may include one or more sensors configured to produce one or more signals in response to the presence of sulfur. Analyzer 210 may further be configured to interact with computer 212 to display and/or communicate the sulfur readings, e.g., communicate to a user via a graphical user interface. Computer 212 may include any conventional processing device configured to receive one or more inputs, e.g., inputs indicative of the sulfur readings, from analyzer 210 and display, e.g., numerical or graphically represent, data indicative of the amount of sulfur measured by analyzer 210. It is contemplated that computer 212 may also be configured to control one or more operations of analyzer 210, system 200, and/or apparatus 100.

INDUSTRIAL APPLICABILITY

The disclosed calibration system may be applicable to any system configured to measure oil consumption. Calibration apparatus 100 and method 300 may provide a more accurate measurement of oil consumption. Additionally, by interconnecting apparatus 100 to system 200, the calibration sample may be analyzed within the same environment in which system 200 may operate to measure the amount of oil consumed by source 202. As such, the calibration sample may be treated substantially similar as exhaust 204 minimizing any potential experimental errors. The operation of apparatus 100 with system 200 will be explained below with reference to FIG. 2.

Figure 2:
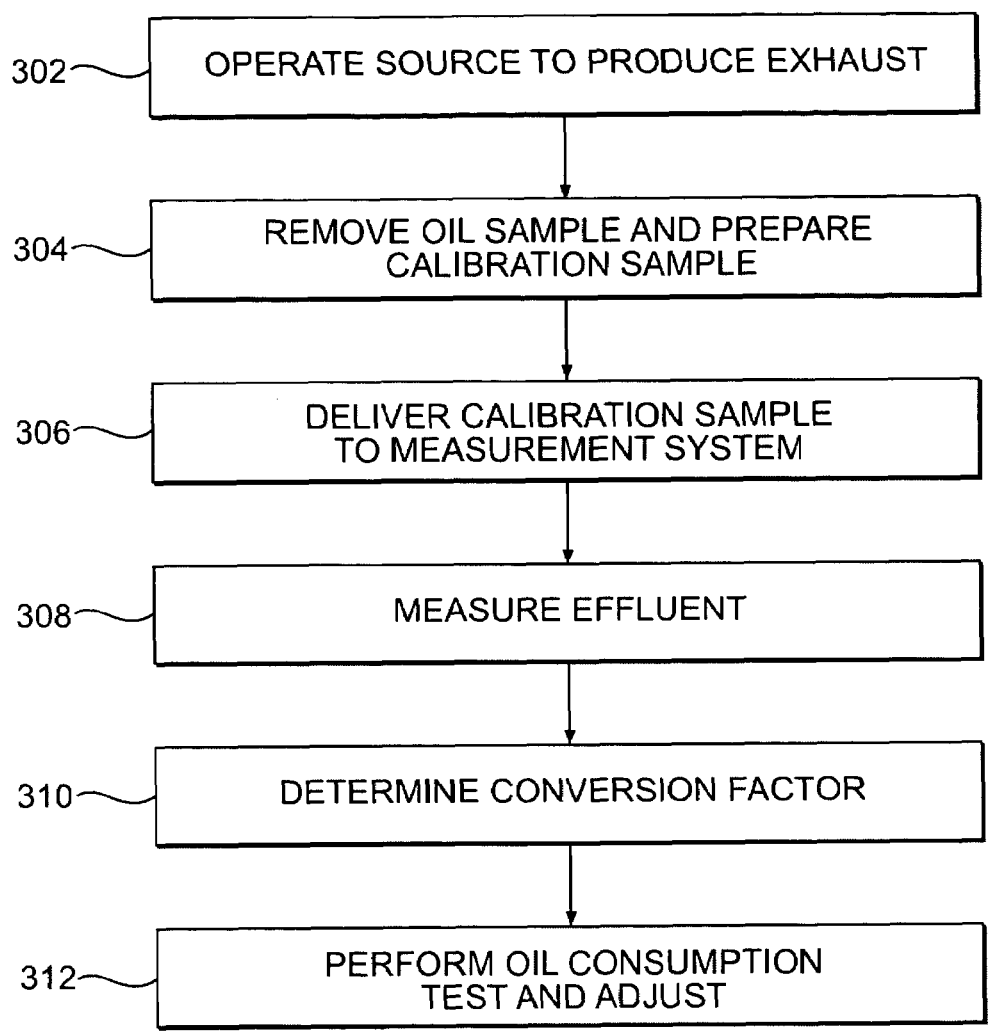
FIG. 2 is a diagrammatic flowchart of an exemplary method for operating the calibration system of FIG. 1.

FIG. 2 illustrates an exemplary method 300 for calibrating system 200. Method 300 may be performed at any time with respect to operation of source 202. For example, source 202 may be operated for a predetermined amount of time, e.g., one or more hours, at predetermined conditions, e.g., 100% load or idle, to reach a steady-state operation. It is contemplated one or more sequences of method 300 may be performed, e.g., 3 to 7 sequences, and that the one or more sequences may be performed at regular or varied intervals, e.g., 4 times per hour. It is also contemplated that multiple sequences of method 300 may be performed to establish a coefficient of variance between results that is within a predetermined range and/or below a predetermined threshold.

Step 302 may include operating source 202 to produce exhaust. Specifically, if source 202 is a combustion engine, step 302 may include supplying fuel and air to the one or more combustion chambers, combusting the fuel, and producing exhaust 204 as the by-product of the combustion. It is contemplated that step 302 may include operating source 202 on a test stand with a connected load, e.g., within a laboratory environment, may include operating source 202 connected to a fixed or mobile machine, e.g., a vehicle, in a non-laboratory environment, e.g., a job site, and/or may include operating source 202 in any environment and at any location.

Step 304 may include removing an oil sample and preparing the calibration sample. Specifically, step 304 may include removing a portion of the oil contained within source 202. For example, a discrete amount of oil may be drained from source 202 and placed within vessel 102 or a continuous flow of oil may be drained from source 202 and communicated to vessel 102. Step 304 may also include adding one or more diluents to the oil sample. Specifically, step 304 may include combining and mixing the sample oil and the one or more diluents to establish the calibration sample. It is contemplated that the oil sample may be removed at any time relative to performing step 302, e.g., operating source 202. It is also contemplated that step 304 may include removing any amount of sample oil from source 202 and combining any amount of diluents with the sample oil, for example, 50 parts diluents to 1 part oil.

Step 306 may include delivering the calibration sample to system 200. Specifically, step 306 may include communicating the calibration sample contained within vessel 102 toward system 200 via pump 104, flow controller 106, and coupler 110. The calibration sample may be directed into system 200 and, in particular, into passageway 214. It is contemplated that step 306 may include delivering any amount of the calibration sample to system 200 at any flow and/or mass rate.

Step 308 may include measuring the sulfur. A portion of exhaust 204 may be diverted via valve 206, the diverted exhaust may entrain and/or mix with the calibration sample delivered via coupler 110 and the diverted exhaust and calibration sample may be directed toward combustion chamber 208. Combustion chamber 208 may include burning the diverted exhaust and calibration sample and the burnt by-products may be directed from combustion chamber 208 toward analyzer 210. Step 304 may include operating analyzer 210 to measure the sulfur and/or sulfur components contained within the burnt by-products, the readings of which may be communicated via one or more inputs to computer 212 for interpretation and/or further manipulation by a user. It is contemplated that step 304 may include measuring the sulfur of the diverted exhaust alone and subsequently measuring the sulfur of the diverted exhaust and the calibration sample. It is also contemplated that step 304 may include establishing multiple readings indicative of the measured sulfur for the diverted exhaust alone and/or the diverted exhaust and the calibration sample and may include establishing multiple readings for several different calibration samples, as is know in the art of experimental testing.

Figure 3:
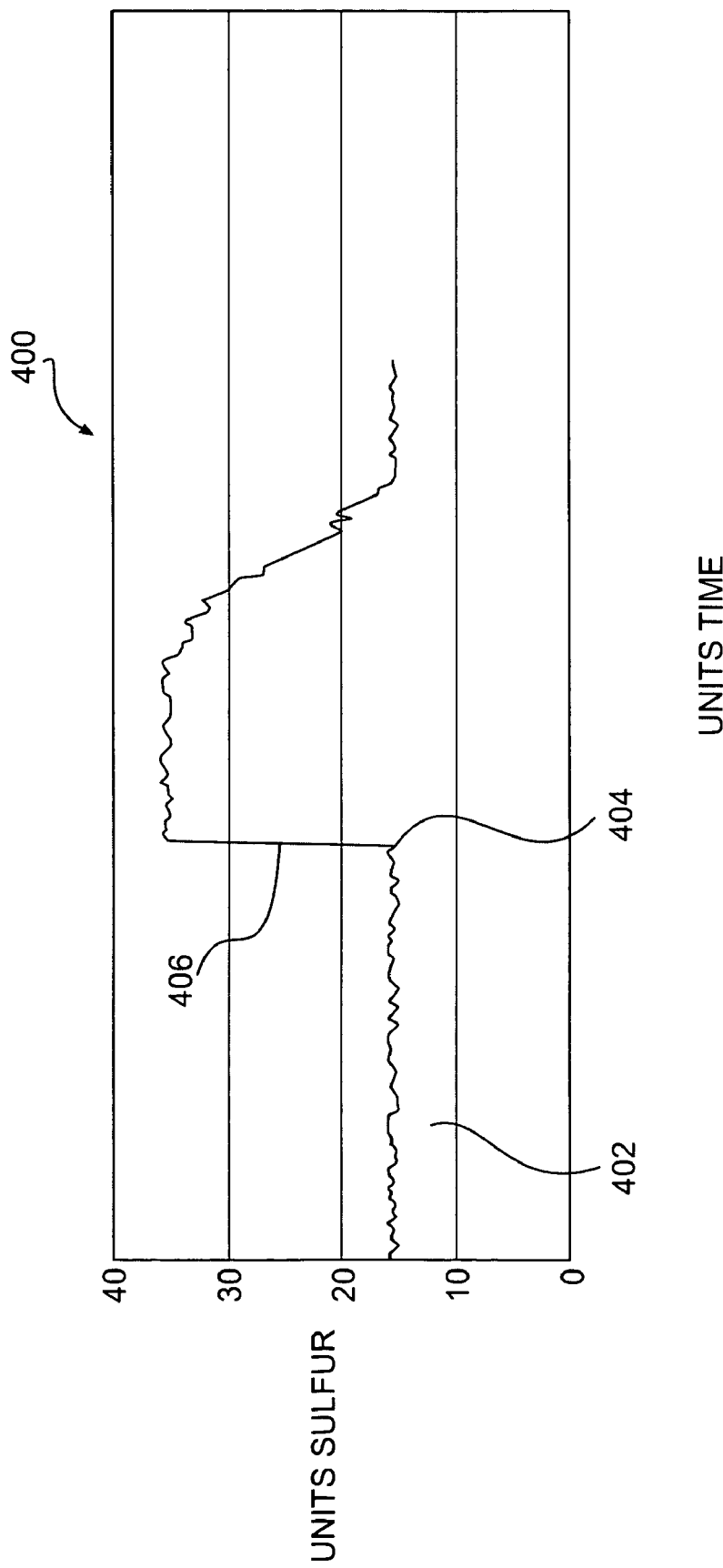
FIG. 3 is a diagrammatic illustration of an exemplary graphical output for a sequence of the method of FIG. 2.

Step 310 may include determining the conversion factor, e.g., a calibration coefficient. Specifically, step 312 may include calculating a difference between sulfur readings measured by analyzer 210 for the diverted exhaust and the combined diverted exhaust and calibration sample. That is, the difference between the amount of sulfur measured by analyzer 210 of the exhaust alone and the exhaust with the added oil-sample mixture. FIG. 3 illustrates a hypothetical example of a plurality of readings established by analyzer 210. For example, during a first period of time 402, the analyzer measures approximately 15 units of sulfur corresponding to the diverted exhaust alone and at time 404 the analyzer measures approximately 35 units of sulfur corresponding to the diverted exhaust and the calibration sample. Time 404 may correspond to the time an amount of calibration sample was communicated to system 200 via coupler 110 and may be established. As such, step 310 may establish the conversion factor as approximately 20 units of sulfur, e.g., indicative of a difference 406 corresponding to the change in measured sulfur. For example, if 1 part of calibration sample produced approximately a difference in measured sulfur of 20 units, it could be assumed that there are 20 units of sulfur per 1 part of calibration sample. Because the calibration sample contains a known amount of sample oil and the diluents can be assumed to not contain sulfur, a difference in measured sulfur of 20 units could also be assumed to indicate that there are 20 units of sulfur per 1 part of oil.

Step 312 may include performing an oil consumption test and adjusting the results thereof as a function of the conversion factor. Specifically, a portion of exhaust 204 may be diverted via valve 206, combusted within combustion chamber 208, and the combusted exhaust may be directed to analyzer 210. Analyzer 210 may measure the sulfur within the combusted exhaust gas. Step 312 may also include correlating the measured sulfur as a function of the conversion factor to determine the amount of oil consumed by source 202 to product the measured sulfur. For example, if analyzer 210 measures 0.5 units of sulfur from the oil consumption test, e.g., diverted exhaust gas without the addition of the calibration sample, and the conversion factor is 1 unit of oil for 20 units of sulfur, step 304 may include determining that source 202 consumes approximately 0.025 units of oil. It is contemplated that the conversion factor and the results of the oil consumption test may be related according to any units and may be determined as a rate of sulfur measured and/or a rate of oil consumed per unit time as a function of the production rate of exhaust 204 by source 202, the flow rate and amount of exhaust 204 diverted via vale 206, the flow rate and amount of the calibration sample delivered to system 200 via coupler 110, and/or one or more conversion factors, constants, and/or mathematical relations known in the art.

Because the calibration sample includes oil utilized by source 202 and apparatus 100 and system 200 produce a calibration amount of sulfur instead of merely testing analyzer 210 with a known amount of sulfur dioxide, the conversion factor determined via method 300 may allow for more accurately determining the amount of oil consumed by source 202. Additionally, because apparatus 100 and system 200 may be connected to source 202, the conversion factor and the amount of consumed oil can be determined within the same environment and thus exposed to the same environmental factors which may influence the measured sulfur.

It will be apparent to those skilled in the art that various modifications and variations can be made to the disclosed calibration system. Other embodiments will be apparent to those skilled in the art from consideration of the specification and practice of the disclosed method and apparatus. It is intended that the specification and examples be considered as exemplary only, with a true scope being indicated by the following claims and their equivalents.

What is claimed is:

1. A method for calibrating a system configured to analyze exhaust gas produced by a fluid consuming source, comprising:
    directing a first flow of exhaust gas toward an analyzer, the analyzer configured to measure at least one component;
    establishing a first value indicative of a measurement of the at least one component within the first flow of exhaust gas;
    removing a first quantity of fluid from the fluid consuming source;
    delivering a second quantity of fluid into the first flow of exhaust gas, the second quantity of fluid being a portion of the first quantity of fluid;
    at least partially combusting the first flow of exhaust gas and the first quantity of fluid upstream of the analyzer;
    establishing a second value indicative of a measurement of the at least one component within the exhaust gas and the at least a portion of the first quantity of fluid; and
    calculating a calibration coefficient for the system as a function of a difference between the first value and the second value.

2. The method of claim 1, further including:
    subsequently directing a second flow of exhaust gas toward the analyzer;
    establishing a third value indicative of a measurement of the at least one component within the second flow of exhaust gas; and
    determining an amount of fluid consumed by the source as a function of the third value and the calibration coefficient.

3. The method of claim 1, wherein the fluid consuming source is a combustion engine and the fluid is oil selectively supplied to the combustion engine.

4. The method of claim 1, wherein the at least one component is sulfur or a sulfur containing compound.

5. The method of claim 1, further including diluting the second quantity of fluid with a diluent and delivering the diluted second quantity of fluid into the first flow of exhaust gas.

6. The method of claim 1, further including operating the source for a predetermined period of time before removing the first quantity of fluid.

7. The method of claim 1, wherein the source is operatively connected to and configured to selectively supply power to a mobile machine.

8. A system for calibrating a measurement system operatively connected to a source producing exhaust and configured to direct a portion of the exhaust toward an analyzer to detect at least one component of the exhaust, the system for calibrating comprising:
    a vessel configured to contain a sample volume of fluid;
    a pump configured to pressurize the sample volume of fluid;
    a coupling configured to fluidly connect the system for calibrating to the measurement system;
    a flow controller configured to control the quantity of fluid communicated from the pump toward the coupling; and
    a fluid passageway fluidly communicating the vessel, the pump, the coupling, and the flow controller.

9. The system of claim 8, wherein the at least one component includes sulfur or a sulfur containing compound.

10. The system of claim 8, wherein the measurement system further includes a combustion chamber and the flow controller is configured to control a rate at which the volume of sample fluid is communicated through the coupler and toward the combustion chamber.

11. The system of claim 8, wherein the sample volume of fluid includes a fluid removed from the source.

12. The system of claim 11, wherein the sample volume of fluid further includes at least one diluent mixed with the fluid removed from the source.

13. The system of claim 11, wherein the source is a combustion engine and the fluid removed from the source is oil used by the engine.

14. A method comprising:
    producing a substantially constant exhaust via the engine;
    selectively diverting a portion of the exhaust via a first valve to establish a first exhaust flow;
    directing the first exhaust flow toward an analyzer;
    establishing a first value indicative of an amount of sulfur or sulfur compounds within the first exhaust flow via the analyzer;
    selectively removing a first volume of oil from the engine;
    pressurizing a second volume of oil via a pump to establish a first oil flow, the second volume of oil including at least a portion of the first volume of oil;
    directing the first oil flow into the first exhaust flow via a coupler and communicating the first oil flow and the first exhaust flow toward a combustion chamber;
    combusting at least a portion of the first oil flow and at least a portion of the first exhaust flow within the combustion chamber to establish a combined flow;
    communicating the combined flow to the analyzer and establishing a second value indicative of an amount of sulfur or sulfur compounds within the combined flow via the analyzer; and
    determining a calibration coefficient for a system as a function of a difference between the first value and the second value.

15. The method of claim 14, further including establishing the calibration coefficient as a function of a ratio between the second value and the second volume of oil.

16. The method of claim 14, wherein the second volume of oil further includes a volume of at least one diluent.

17. The method of claim 14, wherein the engine is operatively connected to one or more components of a mobile machine.

18. The method of claim 14, further including producing the substantially constant exhaust via the engine for a predetermined period of time before selectively diverting the first exhaust flow.

19. The method of claim 14, further including:
    ceasing to direct the first oil flow into the first exhaust;
    selectively diverting a portion of the exhaust via the first valve to establish a second exhaust flow;
    directing the second exhaust flow toward an analyzer; and
    establishing at least one third value indicative of an amount of sulfur or sulfur compounds within the second exhaust flow via the analyzer.

20. The method of claim 19, further including determining a first amount of oil as a function of the third value and the calibration coefficient.

* * * * *